(12) United States Patent
Knafel et al.

(10) Patent No.: US 12,074,943 B2
(45) Date of Patent: Aug. 27, 2024

(54) TECHNIQUES FOR PROVIDING DATA PACKAGES TO ANALYTICAL DEVICES

(71) Applicant: Roche Diagnostics Operations, Inc., Indianapolis, IN (US)

(72) Inventors: Andrzej Knafel, Walchwil (CH); Thomas Weingartner, Allenwinden (CH); Benno Christian Trautmann, Ennetbuergen (CH); Daniel Howorth, Dunoon (AU); Hartmut Mastall, Schliengen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/880,457

(22) Filed: May 21, 2020

(65) Prior Publication Data
US 2020/0382599 A1    Dec. 3, 2020

(30) Foreign Application Priority Data
May 29, 2019    (EP) ..................................... 19177373

(51) Int. Cl.
*H04L 67/12*    (2022.01)
*G06F 8/65*    (2018.01)
(Continued)

(52) U.S. Cl.
CPC ................ *H04L 67/12* (2013.01); *G06F 8/65* (2013.01); *H04L 12/66* (2013.01); *H04L 41/0813* (2013.01)

(58) Field of Classification Search
CPC .. G06F 8/61; G06F 8/65; G16H 40/40; H04L 12/66; H04L 41/0813; H04L 67/12;
(Continued)

(56) References Cited

U.S. PATENT DOCUMENTS 7,974,958 B2 *  7/2011  Ebert ................. G06Q 10/0631
                                                    707/694
10,069,937 B2    9/2018  Hansen
(Continued)

OTHER PUBLICATIONS

Taylor, Anita, Windows Server Update Services 3.0, SP2 Deployment Guide, 2009, 129 pp., retrieved from the Internet Oct. 30, 2019.
(Continued)

*Primary Examiner* — June Sison
(74) *Attorney, Agent, or Firm* — Roche Diagnostics Operations, Inc.

(57) ABSTRACT

A hospital or laboratory network including analytical devices for performing in-vitro diagnosis and a gateway is proposed. The network is configured to send a data package request including information regarding the analytical devices from the gateway to a remote service platform, receive from the remote service platform information regarding available data packages, determine a selection of the available data packages to be downloaded from the remote service platform specific to the analytical devices in the network, request the selection of the available data packages from the remote service platform, download the requested selection of the available data packages from the remote service platform, and provide the requested selection of the available data packages to the analytical devices.

19 Claims, 2 Drawing Sheets

(51) Int. Cl.
  *H04L 12/66* (2006.01)
  *H04L 41/0813* (2022.01)
(58) Field of Classification Search
  CPC . H04L 67/28; H04L 67/2828; H04L 67/2833; H04L 67/34
  See application file for complete search history.

(56) References Cited

U.S. PATENT DOCUMENTS

| | | | | |
|---|---|---|---|---|
| 2003/0036683 A1* | 2/2003 | Kehr | ................ | G06F 21/6245 600/300 |
| 2003/0148530 A1* | 8/2003 | Lauks | ................ | G01N 33/49 436/811 |
| 2005/0144616 A1* | 6/2005 | Hammond | ................ | G06F 8/65 717/173 |
| 2007/0027506 A1* | 2/2007 | Stender | ................ | G16H 40/40 607/60 |
| 2007/0143390 A1* | 6/2007 | Giambalvo | ................ | G06F 8/65 709/200 |
| 2009/0282131 A1* | 11/2009 | Maschke | ................ | H04L 12/40013 709/220 |
| 2011/0246215 A1* | 10/2011 | Postma | ................ | G16H 10/40 705/28 |
| 2012/0297487 A1* | 11/2012 | Xia | ................ | G06F 21/10 726/26 |
| 2013/0036210 A1* | 2/2013 | Birtwhistle | ................ | G16H 40/40 709/221 |
| 2013/0036415 A1* | 2/2013 | Birtwhistle | ................ | G06F 8/65 717/173 |
| 2013/0132109 A1* | 5/2013 | Mruthyunjaya | ................ | G16H 70/60 705/2 |
| 2013/0346108 A1* | 12/2013 | Kamen | ................ | G16H 40/67 705/2 |
| 2014/0180711 A1* | 6/2014 | Kamen | ................ | G16H 70/40 705/2 |
| 2014/0266783 A1* | 9/2014 | Carnes | ................ | H04Q 9/02 340/870.03 |
| 2015/0074176 A1* | 3/2015 | Hansen | ................ | G06F 16/95 709/203 |
| 2017/0286637 A1* | 10/2017 | Arrizza | ................ | A61M 5/142 |
| 2019/0028332 A1* | 1/2019 | Ding | ................ | H04L 43/10 |
| 2021/0074417 A1* | 3/2021 | Pierson | ................ | H04L 67/34 |

OTHER PUBLICATIONS

Taylor, Anita, Windows Server Update Services 3.0, SP2 Operations Guide, 2009, 151 pp., retrieved from the Internet Oct. 29, 2019.

* cited by examiner

TECHNIQUES FOR PROVIDING DATA PACKAGES TO ANALYTICAL DEVICES

CROSS-REFERENCE TO RELATED APPLICATIONS

This application claims priority to EP 19177373.8, filed May 29, 2019, which is hereby incorporated by reference.

BACKGROUND

The present disclosure generally relates to methods and apparatus for providing data packages of a plurality of analytical devices in a network.

There is a growing demand for integrating analytical devices such as in-vitro analyzers employed in hospital or laboratory environments in a network environment. This can be useful to control the analytical devices but also to update or install software on the analyzers (or to relay other data packages to be "consumed" by an analytical device to the analytical device).

Given the number of analytical devices employed in different networks (and in total), the number of software or other data packages that has to be delivered can be high. The number of data packages can be further increased as the (control) software and functionality of the devices becomes more and more complex, which can also drastically increase a number and size of data packages to be relayed to the analytical devices. Moreover, security patches and functional updates might have to be deployed relatively frequently.

As a result, distributing and processing the data packages can be quite complex and resource intensive. For example, a typical large hospital network including a plethora of analytical devices can cause a substantive amount of network traffic due to data packages received by the analytical devices. Likewise, managing and distributing the data packages for a fleet of analytical devices (e.g., tens of thousands or even millions of analytical device) by a remote system of, e.g., a manufacturer of analytical devices might require a considerable amount of resources.

Therefore, there is a need for management of analyzer configuration data at a network level of a network including the analyzers, e.g., at a hospital or laboratory network level (e.g., at a gateway of the network).

SUMMARY

According to the present disclosure, a hospital network or a laboratory network is presented. The network can comprise a plurality of analytical devices for performing in-vitro diagnosis and a gateway connected to the analytical devices. The network can be configured to send a data package request including information regarding the analytical devices from the gateway to a remote service platform, receive from the remote service platform information regarding a plurality of available data packages in reaction to the request, determine, at the gateway, a selection of the plurality of available data packages to be downloaded from the remote service platform specific to the plurality of analytical devices in the network, request the selection of the plurality of available data packages from the remote service platform, download the requested selection of the plurality of available data packages from the remote service platform, and provide the requested selection of the plurality of available data packages to the plurality of analytical devices to update data of the plurality of analytical devices.

Accordingly, it is a feature of the embodiments of the present disclosure to provide management of analyzer configuration data at a network level of a network including the analyzers, e.g., at a hospital or laboratory network level (e.g., at a gateway of the network). Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
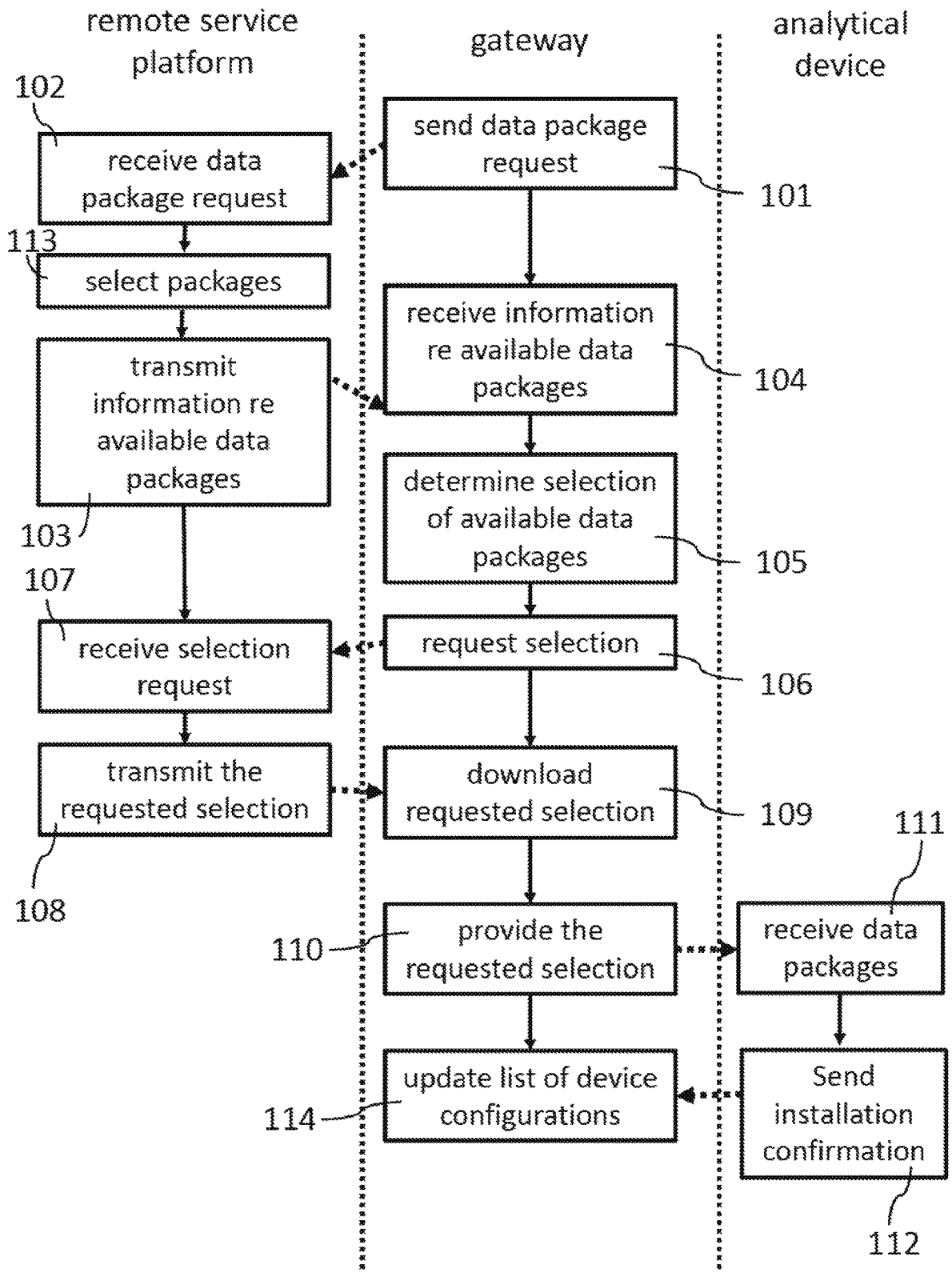
FIG. 1 illustrates a swim lane diagram illustrating the method of providing data packages of a plurality of analytical devices in a network of analytical devices including a gateway according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In one embodiment, a hospital network or a laboratory network including a plurality of analytical devices for performing in-vitro diagnosis and a gateway connected to the analytical devices is presented. The network can be configured to send a data package request comprising information regarding the analytical devices from the gateway to a remote service platform, to receive from the remote service platform information regarding a plurality of available data packages in reaction to the request, and to determine, at the gateway, a selection of the plurality of available data packages to be downloaded from the remote service platform specific to the plurality of analytical devices in the network. The network can further be configured to request the selection of the plurality of available data packages from the remote service platform, download the requested selection of the plurality of available data packages from the remote service platform, and provide the requested selection of the plurality of available data packages to the plurality of analytical devices to update data of the analytical devices. In some embodiments, the data packages data packages can comprise information that can be used in operating the plurality of devices for performing in-vitro diagnosis, e.g., configuration information for a particular test or assay or information related to a particular consumable, e.g., a reagent, calibration material, quality control material and/or any other substance required for carrying out tests or assays at the analytical device.

In another embodiment, a method of providing data packages of a plurality of analytical devices in a network of analytical devices comprising a gateway is presented. The method can comprise sending a data package request including information regarding the analytical devices of the network from the gateway of the network to a remote service platform, and receiving from the remote service platform information regarding a plurality of available data packages in reaction to the request. The method further can comprise determining, at the gateway, a selection of the plurality of available data packages to be downloaded from the remote service platform specific to the plurality of analytical devices in the network, requesting the selection of the plurality of available data packages from the remote service platform and downloading the requested selection of the plurality of available data packages from the remote service platform. The method further can comprise providing the requested selection of the plurality of available data packages to the plurality of analytical devices to update data of the plurality of analytical devices.

In another embodiment, a method of providing data packages of a plurality of analytical devices in a network of analytical devices including a gateway is presented. The method can comprise receiving, at a remote service platform, a data package request including information regarding the analytical devices of the network from the gateway of the network, transmitting from the remote service platform to the gateway information regarding a plurality of available data packages in reaction to the request, receiving, at the remote service platform, a request for a selection of the plurality of available data packages to be downloaded from the remote service platform specific to the plurality of analytical devices in the network, and transmitting the requested selection of the plurality of available data packages to the gateway.

In another embodiment, a computer network is presented. The computer network can comprise a plurality of analytical devices and a gateway connected to the plurality of analytical devices. The computer network can be configured to carry out the steps of the above method.

In another embodiment, a computer system is presented. The computer system can comprise a remote service platform connected to a network. The network can comprise a plurality of analytical devices and a gateway connected to the plurality of analytical devices. The remote service platform can be configured to carry out the steps of the above method.

The techniques of the above embodiments can have advantageous technical effects.

Firstly, the above embodiments can allow the management of analyzer configuration data at a network level of a network including the analyzers, e.g., at a hospital or laboratory network level (e.g., at a gateway of the network). In some prior art solutions, the management of the analyzer configuration data happens remotely and in a centralized manner for all analytical devices managed by a particular entity (e.g., a particular vendor of analytical devices). It has to be understood that the number of devices can go easily into the tens of thousands or hundreds of thousands. This means that central management of configuration data for all of this large number of devices can be challenging and resource-intensive.

Secondly, the selection of data packages at the gateway (i.e., local in a network the analytical devices reside in) can happen on an on-demand basis which can reduce data traffic and resource requirements.

This technique can be scalable as additional networks including analytical devices each having one or more gateways can be added without largely increasing the organizational and computational burden at the remote service platform. This can render the system for distributing data packages more scalable. A centralized solution might not be easily scalable, for example, as a doubling or tripling of the analytical devices might mean that the resources at the central size to manage the analytical devices can be insufficient. The techniques of the present disclosure can shift (at least some) of the processing steps to the networks including the analytical devices (e.g., hospital or laboratory networks).

Thirdly, funneling the data packages through the gateway can have various other advantages in some embodiments. On the one hand, data security can be improved, as the gateway can constitute a defined point of entry for data packages to the network. It may be easier to implement and enforce security measures for this defined point of entry provided by the gateway.

Moreover, data traffic can be reduced as the gateway can organize download of data packages in an efficient manner. For instance, in cases where a particular data package is required for two or more analytical devices in a network, the gateway can download the data package only once. This can reduce the data traffic to the network significantly in some embodiments.

In addition, downloads and distribution of data packages can be conveniently scheduled and organized by using the gateway. For instance, analytical devices having interrupted or irregular connectivity to outside networks (e.g., a remote server) can be more reliably and efficiently provided with data packages by using the gateway. In addition, the gateway can be configured to allow intelligent and versatile distribution of data packages to the analytical devices. In some embodiments, the data packages can be loaded onto removable media and distributed in this form to (some) analytical devices of the network. In other embodiments, the gateway can schedule the distribution of packages to avoid interference with the operation of the analytical devices or to improve productivity of the analytical devices. For instance, the data packages can be distributed during downtime or times of reduced workload of the analytical devices.

The above features may be more difficult to implement when managing data package distribution centrally at prior art remote service platform in some embodiments, or their implementation may cause a considerable amount of additional workload at the remote service platforms.

Last, data packages for each analytical device can be immediately available after being downloaded to the gateway. In some prior art solutions, a particular data package can be distributed to multiple analytical devices in stretched out manner as each device can be provided with the data package by the remote service platform. The distribution of the data packages to the devices by the gateway can be more efficient as it frequently happens over a local area network having higher bandwidth.

Several terms are used as having a particular meaning in the present disclosure.

A "network" in the present disclosure can refer to a plurality of connected devices with data communication capabilities. The connected devices in a network can be designated by being managed by a particular organization. For instance, the network can be a hospital network, a laboratory network, a network of a general practitioner's cabinet or a network of a pharmacy. In some embodiments, the network can be constituted by a set of devices, which form a logical group (e.g., a network of devices of a particular organization as defined above). In addition or alternatively, the devices in a network can be located in relatively close spatial relationship (e.g., a campus, a laboratory or a hospital building). The devices of the network can be connected by a local area network. However, in other embodiments, the devices of the network can be located at two or more remote locations (e.g., two different sites of a hospital).

The terms "gateway" and "remote service platform" may not impose any limitation to a particular hardware and software configuration. Rather, the gateway and the remote service platform can be any computer system (having suitable hardware and software) configured to provide the functionality defined in the present disclosure. For instance, the gateway and the remote service platform can form part of a more complex management software on premise and at a remote site, respectively.

The term "install" (in the context of data packages) may not be limited to any particular operation of modifying or updating a software of the analytical device. Rather, the term install can encompass any operation in which data included in a data package can be incorporated/deployed in the analytical device (directly or after processing steps such as unpacking or compilation). For example, a data package may include information that is in some way or form used in operating the analytical device. In this situation, installing the data package may mean storing the information at a respective location to make it available to the analytical device. Further embodiments of how data packages can be installed on analytical devices will be discussed below.

An "analytical device" or "analyzer" (the terms can be used interchangeably in the present disclosure) according to the present disclosure can be a—usually at least partially automated—apparatus dedicated to perform an analytical function. In some embodiments, the analytical devices or analyzers can be configured to carry out the analysis of samples (e.g., samples for in vitro diagnostics). For example, an analytical device can be a clinical diagnostics system for performing in-vitro diagnostics.

The analyzers of the present disclosure can have different configurations according to the need and/or according to the desired workflow. Additional configurations may be obtained by coupling a plurality of apparatuses and/or modules together. A "module" can be a work cell, typically smaller in size than the entire analytical device, which can have a dedicated function. This function can be analytical but can be also pre-analytical or post-analytical or it can be an auxiliary function to any of the pre-analytical function, analytical function or post-analytical function. In particular, a module can be configured to cooperate with one or more other modules for carrying out dedicated tasks of a sample processing workflow, e.g., by performing one or more pre-analytical and/or analytical and/or post-analytical steps.

In particular, the analytical devices can comprise one or more analytical modules designed to execute respective workflows that are optimized for certain types of analysis. The analytical device can include analytical apparatuses for one or more of clinical chemistry, immunochemistry, coagulation, hematology, etc.

Thus, the analyzer may comprise one analytical module or a combination of any of such modules with respective workflows, where pre-analytical and/or post analytical modules may be coupled to individual analytical modules or be shared by a plurality of analytical modules. Alternatively, pre-analytical and/or post-analytical functions may be performed by units integrated in an analytical device. The analytical device can comprise functional units such as liquid handling units for pipetting and/or pumping and/or mixing of samples and/or reagents and/or system fluids, and also functional units for sorting, storing, transporting, identifying, separating, and detecting.

The term "sample" can refer to a biological material suspected of containing one or more analytes of interest and whose detection, qualitative and/or quantitative, may be associated to a particular condition (e.g., a clinical condition).

The sample can be derived from any biological source, such as a physiological fluid, including, blood, saliva, ocular lens fluid, cerebral spinal fluid, sweat, urine, milk, ascites mucous, synovial fluid, peritoneal fluid, amniotic fluid, tissue, cells or the like. The sample can be pretreated prior to use, such as preparing plasma from blood, diluting viscous fluids, lysis or the like; methods of treatment can involve filtration, centrifugation, distillation, concentration, inactivation of interfering components, and the addition of reagents. A sample may be used directly as obtained from the source in some cases or following a pretreatment and/or sample preparation workflow to modify the character of the sample, e.g., after adding an internal standard, after being diluted with another solution or after having being mixed with reagents e.g., to enable carrying out one or more in vitro diagnostic tests, or for enriching (extracting/separating/concentrating) analytes of interest and/or for removing matrix components potentially interfering with the detection of the analyte(s) of interest.

The term "sample" can be used to indicate a sample before sample preparation whereas the term "prepared sample" can be used to refer to samples after sample preparation. In non-specified cases, the term "sample" may generally indicate either a sample before sample preparation or a sample after sample preparation or both. Examples of analytes of interest are vitamin ID, drugs of abuse, therapeutic drugs, hormones, and metabolites in general. The list is, however, not exhaustive.

In particular, the analytical device can comprise a sample preparation station for the automated preparation of samples. A "sample preparation station" can be a pre-analytical module coupled to one or more analytical apparatuses or a unit in an analytical apparatus designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing and the like.

A "consumable" can be any disposable item that can be used and replenished on a regular basis during operation of the analytical device. For example, a consumable may include reagents or other substances required for carrying out tests or assay's at the analytical device. In other embodiments, consumables can include hardware, which is only used once or a limited amount of times (e.g., reaction vessels or other types of vessels or instrument tips).

A "reagent" can be a substance used for treatment of a sample in order e.g., to prepare a sample for analysis, to enable a reaction to occur, or to enable detection of a physical parameter of the sample or analyte contained in the sample. In particular, a reagent can be a substance that can be or can comprise a reactant, typically, a compound or agent capable e.g., of binding to or chemically transforming one or more analytes present in a sample or an unwanted matrix component of the sample. Examples of reactants are enzymes, enzyme substrates, conjugated dyes, protein-binding molecules, ligands, nucleic acid binding molecules, antibodies, chelating agents, promoters, inhibitors, epitopes, antigens, and the like. However, the term reagent can be used to include any fluid that can be added to a sample including a dilution liquid, including water or other solvent or a buffer solution, or a substance that can be used for disruption of specific or nonspecific binding of an analyte to a protein, binding proteins or surfaces.

Samples may be provided, for example, in sample containers such as sample tubes, including primary tubes and secondary tubes, or multi-well plates, or any other sample carrying support. Reagents may be arranged, for example, in the form of containers or cassettes containing individual reagents or group of reagents and placed in appropriate receptacles or positions within a storage compartment or conveyor. Other types of reagents or system fluids may be provided in hulk containers or via a line supply.

Unless specified differently in the respective context, the terms "about" in connection with values for parameters can mean to include a deviation of +/−10% from the specified value in the present disclosure.

General Overview

FIG. 1 is a swim lane diagram illustrating the method of providing data packages of a plurality of analytical devices in a network of analytical devices including a gateway according to the present disclosure.

As can be seen, FIG. 1 separates between steps performed at a remote service platform (left side), a gateway (middle), and one analytical device (right side). As can be seen, the teachings of the present disclosure can include modifications of one or more of the remote service platform, the gateway and the analytical device. Accordingly, the present disclosure is not limited to a system including all three (or two selected ones) of these entities but also is directed at each of the entity in isolation being configured to carry out the respective steps of the present disclosure. For example, a gateway can be implemented to carry out the gateway-related steps of the present disclosure and can be implemented without necessarily being limited to a system also including a remote service platform.

Therefore, the techniques of the present disclosure will be discussed from different viewpoints subsequently. The discussion will start with the gateway.

As can be seen in the middle column, the technique can comprise sending 101 a data package request including information regarding the analytical devices of the network from the gateway of the network to a remote service platform. The technique can further comprise receiving 104 from the remote service platform information regarding a plurality of available data packages in reaction to the request.

In other words, the technique of the present disclosure can implement a pull-scheme in which the data package request can initially be sent from the gateway of the network including the analytical devices to the remote service platform, and not vice versa. This does not mean, however, that there is no communication between the remote service platform and the gateway prior to the request. For instance, the remote service platform can periodically or upon occurrence of a particular event inform the gateway that there are new data packages. However, the remote service platform may not initiate the process of distributing the data packages (i.e., there is no push-mode distribution of the data packages according to the present disclosure).

In a further step, the technique of the present disclosure can comprise determining 105, at the gateway, a selection of the plurality of available data packages to be downloaded from the remote service platform specific to the plurality of analytical devices in the network and requesting 106 the selection of the plurality of available data packages from the remote service platform.

In this manner, the remote service platform may not have to do the "heavy lifting" regarding selecting which data packages can be downloaded for further distribution to the analytical devices of a particular network. Rather, the management of which data packages are required (e.g., missing) can happen to a large(r) extent at the gateway (there selection of the data packages may still comprise a substantive amount of processing operations at the remote service platform, as described below).

The technique can continue with downloading 109 the requested selection of the plurality of available data packages from the remote service platform and providing 110 the requested selection of the plurality of available data packages to the plurality of analytical devices to update data of the plurality of analytical devices.

The different steps carried out at the gateway will be discussed in more detail subsequently.

The step of sending a request for a plurality of applicable data packages 101 from the gateway can be triggered in several different ways. In some embodiments, the request can be sent according to a particular schedule (e.g., regularly such as once per day or once per week). In other embodiments, the sending can be triggered on demand. For example, an operator can trigger sending the request in some embodiments. In addition or alternatively, the sending can be triggered by one or more events. These events can include one or more of a change in configuration of one or more analytical devices of the network (e.g., adding a module to an analytical device or adding an assay to an analytical device) and an adding of one or more analytical devices to the network. Moreover, the event can be a data transmittal from the remote service platform (e.g., a message that new data packages are available).

In some embodiments, the information regarding the analytical devices of the network included in the data package request can be a part of gateway configuration information or device configuration information.

The information regarding the analytical devices included in the request can include any information suitable to identify a set of analytical devices or set of classes or types of analytical devices in the network of analytical devices (e.g., a unique identifier of each analytical device or a unique identifier for each type or class of analytical devices in the network).

For instance, the information regarding the analytical devices can include one or more of information regarding types of class of the devices, information regarding the geographical location of the network, information regarding a language of the network or the analytical devices, information regarding a software or hardware configuration of the analytical devices, information regarding installed consumables of the devices (e.g., reagents, calibration/quality control materials) and information regarding installed assays (test protocols). In addition or alternatively, the information regarding the analytical devices can include inventory information regarding the data packages installed on one or more analytical devices.

In some examples, the gateway can maintain device configuration information for each of the plurality of analytical devices in the network (which can be sent (completely or partially) as part of the data package request.

The information regarding the analytical devices can include device metadata for each analytical device. For instance, the device metadata can include one or more of a device identifier, a gateway identifier identifying a gateway the analytical device is connected to, location metadata identifying a location of the analytical device and language metadata indicating a target language for the analytical device, and a module identifier identifying one or more modules of the respective analytical device. In other embodiments, the device configuration information can include different types of device metadata.

The gateway can update the information regarding the analytical devices, e.g., when a new data package is installed on a particular device or when another change in the configuration of the particular analytical device takes place.

Moreover, the gateway configuration information can include information characterizing the gateway. The gateway configuration information can include one or more of a list of analytical devices connected to the gateway, a list of analytical devices modules present in the network of the gateway, location metadata identifying a location of the gateway and language metadata indicating a language setting of the gateway. The gateway can update the gateway configuration information, e.g., when a new data package is distributed, when the set analytical devices or modules changes or when other configurations or settings in the network change.

In other embodiments, device information can be additionally kept at the remote service platform or other centralized repository.

The determination of a selection of available packages can happen in one of several ways (or include a combination of several measures).

In some embodiments, the step of determining a selection of the plurality of available data packages can comprise determining which data packages are required for the plurality of analytical devices in the network. The required data packages can be data packages missing on respective ones of the plurality of analytical devices in the network.

The gateway can evaluate the information regarding a plurality of available data packages received from the remote service platform (e.g., a list of available data packages). This can include comparing the available data packages with a list of data packages, which are installed on the analytical devices (e.g., a list of data packages, which are installed on each analytical device of the analytical devices of the network). Based on the comparison operation, the gateway can determine the selection of the data packages.

In addition or alternatively, determining which data packages are required can comprise evaluating one or more rules defined at the gateway. The nature of the rules can be quite wide-ranging.

In some embodiments, the rules can be user-defined. Additionally or alternatively, the rules can define one or more requirements for the data packages. For instance, the requirements can relate to one or more of a source of the data packages. In addition, or alternatively, the requirements can relate to location of the network (e.g., a region or country). In addition, or alternatively, the requirements can be a language requirement.

The selection of the plurality of available data packages can comprise less than all data packages. In some embodiments, the selection can include substantially less than all data packages (e.g., less than 50% or less than 10% of all data packages). In this manner, the gateway can use the available information regarding the analytical devices of its network to reduce a number of data packages that have to be downloaded from the remote service platform.

The step of downloading the data packages will be discussed next. In some embodiments, each data package is only downloaded by the gateway once regardless of a number of analytical devices in the network the data package is to be installed on. In this context, the expression "each data package" can refer to different types of data packages. For example, a particular type of analytical device might be present multiple times in a network (e.g., a hospital network or a laboratory network). At some point in time, a particular data package can be distributed to each of the multiple analytical devices of the same type. Then, the data package might be only downloaded once by the gateway (and then relayed to the multiple analytical devices). In some prior art systems, each analytical device might be individually provided with the respective data package (e.g., from a remote server which can increase data traffic).

In some embodiments, the selection of the plurality of available data packages can be received from the remote service platform as a batch. Alternatively, the selection of the plurality of data packages can be received in multiple batches or on-by-one.

After the data packages have been received at the gateway, the selection of data packages can be distributed 110 to the analytical devices. In some embodiments, this can include scheduling, at the gateway, the distribution of the received selection of the plurality of available data packages to the plurality of analytical devices according to one or more rules.

For instance, the rules can include a rule forcing a staggered distribution of data packages to analytical devices of the same type to ensure that at least one device of the type is available at a given time.

For example, the type of analytical devices can be an analytical device providing a particular analytical function (e.g., a particular assay or test in-vitro or on the human body). The gateway can secure that at least one of these devices can be available at each point in time in the network (e.g., the hospital network or the laboratory network) by scheduling the distribution of data packages to the analytical devices in a staggered manner. In this manner, interference with the operation of the device due to installation or after installation of the respective data package can be avoided. In some embodiments, the data packages can be distributed to the analytical devices of the same type in a non-overlapping manner.

In addition or alternatively, the rules can include a rule scheduling a distribution to the analytical devices taking into account an idle state and/or a workload of the analytical devices. For example, the data packages can be distributed at night or during an off-time of the perspective analytical device. In addition or alternatively, the data packages can be distributed when a workload of the analytical device is low (e.g., when the respective analytical device is idle).

In other embodiments, the distribution of the data packages to the analytical devices can be triggered by a data package request from the analytical devices (i.e., a pull-mode instead of a push-mode in which the distribution is triggered by the gateway).

The main steps of the method of providing data packages of a plurality of analytical devices have been discussed above. Further aspects of these steps will be discussed below (in particular in the context of FIG. 2).

Further Steps

The method of providing data packages of a plurality of analytical devices can include several further steps.

In some embodiments, the gateway can update 114 the device configuration information (or the inventory information) after having provided the selection of data packages to the analytical devices of the network. This can include checking an installation confirmation that the respective data package has been installed on a particular analytical device. In some embodiments, the respective analytical device can send 112 the installation confirmation to the gateway.

In further embodiments, the gateway can send the device configuration information (or a processed version thereof), or the inventory information, to a remote location (not shown in FIG. 1). The remote location can be a location of a source or distributor of the data packages (e.g., a supplier of the analytical devices and/or service operator involved in servicing and maintaining the analytical devices).

In addition or alternatively, the gateway can provide information indicating the received selection of the plurality of available data packages to a remote location (not shown in FIG. 1). The remote location can be a location of a source or distributor of the data packages (e.g., a supplier of the analytical devices and/or service operator involved in servicing and maintaining the analytical devices).

In this manner, the gateway can make the information collected at the gateway accessible to other entities where they can be used in developing or distributing data packages or analytical devices, or for other functions related to operating the analytical devices.

Technique as Seen from Remote Service Platform

FIG. 1 also illustrates the method of providing data packages of a plurality of analytical devices as seen from the remote service platform (left side).

As discussed above, the present disclosure can also relate to techniques performed at the remote service platform. Even though the remote service platform can communicate with the gateway in the techniques of the present disclosure, the present disclosure can also relate to the remote service platform and the methods carried out thereon.

Returning to FIG. 1, the remote service platform can receive 102 a data package request from the gateway of the network including information regarding the analytical devices of the network.

The remote service platform can transmit 103 to the gateway information regarding a plurality of available data packages in reaction to the request. In a further step, the remote service platform can receive a request for a selection of the plurality of available data packages to be downloaded from the remote service platform specific to the plurality of analytical devices in the network. Then, the remote service platform can transmit 108 the requested selection of the plurality of available data to the gateway.

Numerous embodiments of these steps have already been discussed above in connection with the actions of the gateway which in some cases performs sending operations corresponding to the receiving operations at the remote service platform, and vice versa. The above-discussed features can also be employed on the remote service platform. Therefore, the subsequent discussion will focus on the remote service platform specific embodiments.

In some embodiments, the remote service platform can use the information regarding the analytical devices of the network (which can any of the information discussed above) to select 113 the plurality of available data packages to be downloaded from the remote service platform.

This can include processing data package metadata received from a data package source (not shown in FIG. 1 and described in more detail below) and the information regarding the analytical devices of the network to select the plurality of available data packages. The remote service platform can compare the data package metadata with corresponding information regarding the analytical devices received with the data package request and select data packages matching the information regarding the analytical devices.

For instance, the data package metadata received from a data package source might include metadata specifying a language or a target geographical location for a data package. If the information regarding the analytical devices specifies that a set language of an analytical device is English, the remote service platform can select only data packages targeted at analytical devices whose set language is English.

In some embodiments, the remote service platform can filter out already installed data packages based on the inventory information received from the gateway.

In other embodiments, the remote service platform can filter out packages for analytical devices or types of analytical devices, or analytical devices having particular configuration actually present in the network. For instance, a particular network might not include analytical devices on which a particular assay is installed. In this situation, the remote service platform can filter out data packages for this particular assay.

In this manner, the information regarding available data packages can already include a specific selection of data packages selected based on information received from the gateway regarding the particular analytical devices of the network.

Technique as Seen from Analytical Device

As shown in FIG. 1, the analytical device can receive the data packages 111. In some embodiments, the analytical device can be completely or partially agnostic to implementation specifics of the gateway and the remote service platform involved in distributing the data packages. In other embodiments, the analytical devices can carry out certain steps in addition to receiving the data packages.

For example, the analytical device can pull the data package from the gateway and/or set a time for a transmission of the data package from the gateway. In other embodiments, the analytical devices can provide information to the gateway (e.g., regarding a device status such as a workload) to allow the gateway scheduling the distribution of the data packages.

In addition or alternatively, as discussed above, the analytical devices can send installation confirmations 112 to the gateway upon completion of an installation of one or more data packages.

In the preceding sections, multiple embodiments of the method of providing data packages of a plurality of analytical devices in a network have been discussed. In the subsequent sections, further details regarding the data packages and the systems carrying out the methods of the preset disclosure will be discussed in more detail.

Embodiments Relating to the Data Packages

In the preceding sections, the data packages have been discussed in a fairly abstract manner. Indeed, the techniques of the present disclosure are not limited to a particular type of data package. However, several example data packages, which can be distributed using the techniques of the present disclosure, will be discussed in the subsequent sections.

In some embodiments, the data packages can be software packages for the analytical analyzers (or for modules thereof). For instance, the software packages can modify or update an existing software or software module of the analytical device (e.g., a new version of the software or the software module of the analytical device). For example, the data packages can include bug fixes or other error corrections for the software of the analytical devices.

In other embodiments, a data package can include a new software or software module for the analytical device (i.e., to initiate a first installation of a software or software module).

In general, the data packages can include any software component required for setting up or updating any software running on the analytical device.

In still other embodiments, the data package can include configuration information (e.g., a configuration file) for an analytical device. In general, configuration information can include any information used in setting up or changing the setting of an analytical device.

For example, the configuration information can include configuration information for a particular test or assay. In still other examples, the data package can include information related to a particular consumable (e.g., information regarding a reagent/reagent lot or another type of consumable or lot of consumable such as calibration materials or quality control materials). This information can also be considered as configuration information of the analytical device.

In other embodiments, the data package can include configuration information such as language data (or other data, which can be used to change the setup of an analytical device in a particular manner).

In still other embodiments, the data packages can include documentation related to the analytical devices or components thereof such as, for example, an operator's manual in a particular language).

System Setup of an Embodiment

In the preceding sections, numerous details of the methods of the present disclosure have been discussed in some detail. In the subsequent sections, embodiments of the systems carrying out these methods will be discussed in more detail in the context of FIG. 2.

Figure 2:
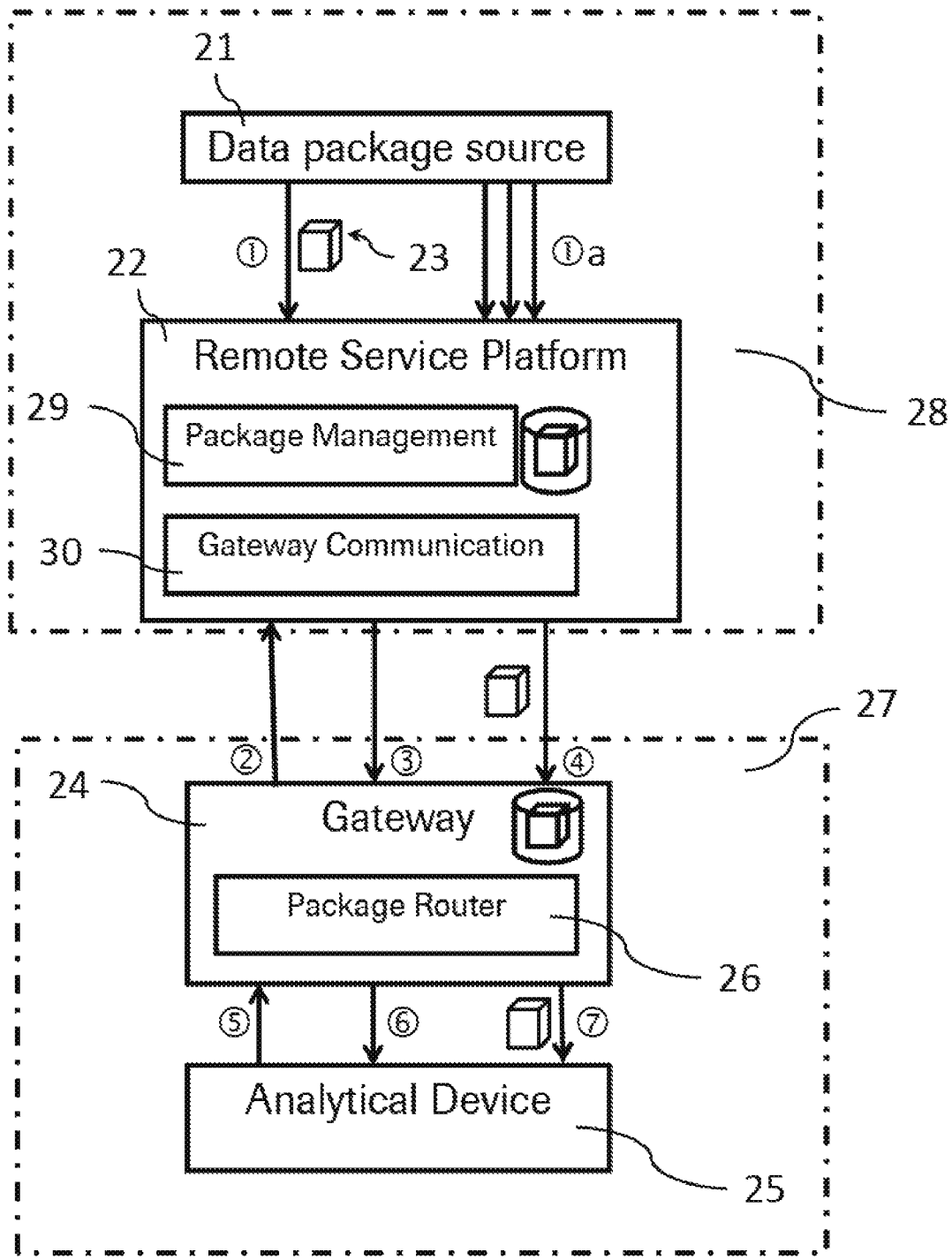
FIG. 2 illustrates a schematic diagram illustrating the elements of the system for distributing data packages according to an embodiment of the present disclosure.

FIG. 2 shows a schematic diagram illustrating the elements of the system for distributing data packages of the present disclosure.

As shown in FIG. 2, a computer network 27 (correspond to the network including the analytical devices discussed above) can comprise a plurality of analytical devices 25 and a gateway 24 connected to the plurality of analytical devices 25. The computer network 27 can be configured to carry out the steps of the techniques described in the present disclosure (that is, in connection with the gateway 24 and the analytical devices 25).

FIG. 2 also shows a computer system 28 comprising a remote service platform 22 connected to the network 27. The remote service platform 22 can be configured to carry out the steps of the methods described in the present disclosure relating to the remote service platform 22.

In some embodiments, as discussed above, the network 27 can be (or can be part of) a hospital network, a laboratory network, a network of a general practitioner's cabinet or a network of a pharmacy. The analytical devices 25 can include any one of the analytical devices discussed above (in any combination and in any number of units).

In the preceding sections, the sub-structure of the gateway 25 and the remote service platform 22 has not been discussed. In fact, the gateway and the remote service platform can be thought of as black boxes in some embodiments, i.e., their respective internal structure can take various forms as long as this internal structure can be configured to carry out the steps of the methods described in the present disclosure.

In the embodiment of FIG. 2, the remote service platform 22 can include a package management module 29 and a gateway communication module 30. In addition, the remote service platform 22 can be connected to a data package source 21. The data package source 21 can be an entity, which can provide data packages 23 to the remote service platform 22, which can subsequently be distributed by the remote service platform 22 and the gateway 24. In some embodiments, the data package source 21 can be a supplier of the analytical devices and/or service operator involved in servicing and maintaining the analytical devices. In still other embodiments, the data package source 21 can be a third party, which can provide software and/or hardware used in the analytical devices. The data package source 21 can be an abstract computer system which can communicate with the remote service platform (e.g., via an internet connection). The remote service platform 22 can be connected to multiple data package sources 21 in some embodiments. In still other embodiments, the remote service platform 22 itself can include act as the data package source 21.

The package management module 29 can keep track of all available data packages, which are supplied by one or more sources. In addition, the package management module 29 can carry out the steps of processing the data package request received from the gateway 24 and selecting the available data packages for a particular set of analytical devices 25 described in the present disclosure.

The gateway communication module 30 can handle reception of all requests from the gateway 24 and providing information and data packages 23 to the gateway 24 as described in the present disclosure.

The gateway 24 can include a package router module 26, which can be configured to handle the data package distribution steps to the analytical devices according to the present disclosure.

In different embodiments, the remote service platform 22 and/or the gateway 24 can include different or additional modules compared to the modules shown in FIG. 2. While a certain setup of the gateway 24 and the remote service platform 22 can be advantageous, the setup can be varied as long as the gateway 24 and the remote service platform 22 can be capable of performing the steps of the techniques of the present disclosure.

Both entities can be embodied in any shape or form for this purpose. For instance, the remote service platform 22 can be located on a remote server and/or the cloud. The remote service platform 22 can be stand-alone entity or part of a more complex software solution also providing other functions. The same can be true for the gateway 24, which can be part of a network management software of the network 27 (e.g., a hospital management software or a laboratory management software). In other embodiments, the gateway 24 can be part of a management software for managing the plurality of analytical devices.

This is also true for the configuration of the communication connection between the remote service platform 22 and the gateway 26, and between the gateway 24 and the analytical devices 25. These network connections can be any communication connection allowing sending and receiving the information and data packages described herein. In one embodiment, the gateway 24 can be connected with the remote service platform 22 through the internet. The network 27 can be a local area network in some examples.

FIG. 2 also illustrates the steps (labelled as (1) to (7)) of the techniques of the method of providing data packages discussed above. Some steps of this method will be discussed in more detail below.

In particular, as discussed above, the data package source 21 can provide (steps (1) and (1)a) data packages 23 for the analytical devices.

In some examples, this can include receiving a particular data package 23 in a first step (1). Data package metadata can be received separately in a second step (1)a. For a particular data package, different (or updated) data package metadata can be received at multiple different times. For instance, a new data package can be released by the data package source 21 and transmitted to the remote service platform 22. At multiple later points in time, data package metadata can be transmitted to the remote service platform (e.g., whenever the data package is released for a particular geographic region, for a particular analytical device or class of analytical devices etc.).

Steps (2), (3), (4) and (7) correspond to the steps discussed in great detail in connection with requesting the data packages 23 from the gateway 24, downloading the data packages to the gateway 24 and distributing the data packages 23 to the analytical devices 25.

Steps (5) and (6) are optional additional steps, which will be discussed subsequently in more detail. In some embodiments, the distribution of the data packages 23 to the analytical devices can happen according to a similar schema as discussed for the provision of data packages 23 from the remote service platform 22 to the gateway 24. In that, the gateway 24 can assume the role of the remote service platform and the analytical device 25 can assume the role of the gateway. The features discussed above and below in this context can equally be applicable for the requesting of data packages by the analytical device 25 or the group of analytical devices.

In particular, the distribution of the data packages can happen in an "upon request"-mode in which a particular analytical device 25 or a group of analytical devices can initiate the data package distribution process. For example, the analytical device 25 can send a data package request to the gateway 24 (step (5)). In addition or alternatively, the gateway 24 can send information regarding a plurality of available data packages for the analytical device 25 in reaction to the request (step (6)). Then, the analytical device 25 can determine a selection of the plurality of available data packages 23 to be downloaded from the gateway 24 specific to the analytical device 25 and request the selection of the plurality of available data packages from the gateway 24.

However, in other embodiments the distribution of the data packages can be carried out in a push mode, i.e., the gateway 24 can initiate the distribution of the data packages 23 to the analytical devices 25. Embodiments of this push mode have been described above in connection with FIG. 1.

Example Embodiment Including Distribution of Information Regarding Calibration Materials (or Other Reagents or Consumables)

In one embodiment, the techniques of the present disclosure can be used to provide data packages including information regarding calibration materials to particular analytical devices for performing in-vitro diagnosis in a network.

The information can be requested from the gateway of the networks of the present disclosure and provided to the particular analytical devices for performing in-vitro diagnosis in the network. In some examples, a plurality of analytical devices for performing in-vitro diagnosis can require multiple calibration materials each associated with a particular function of the respective analytical devices for performing in-vitro diagnosis (e.g., a particular test or assay, a particular measurement type or other functions). Different calibration materials can also be required for calibrating the analytical devices for different concentration levels of a respective analyte in some examples.

Calibration materials can be provided with information specific to a particular calibration material or many calibration materials. The information can be included one or more files (e.g., pdf-files). This information may differ from material to material and/or from lot to lot.

In some examples, calibration materials can be provided with calibrator values indicating measurement results to be expected when processing the calibration device in a particular analytical device for performing in-vitro diagnosis (e.g., when carrying out a particular test or procedure on the analytical device for performing in-vitro diagnosis). These values can be lot-specific or sample-specific. When using the techniques of the present disclosure, the calibrator values can be made available to the particular analytical devices for performing in-vitro diagnosis of the network working with the respective lot.

In some examples, a particular calibration material or a particular lot of calibration materials can be processed on multiple analytical devices for performing in-vitro diagnosis of the network. The techniques of the present disclosure can allow managing the download of this information in a more flexible and efficient manner in some examples, as discussed in the present disclosure. In particular, information regarding particular calibration materials or lots of calibration materials can only be downloaded once (and then distributed to multiple analytical devices for performing in-vitro diagnosis of the network requiring the respective information). If a new calibration material or lot of calibration materials is provided, the techniques of the present disclosure can allow for only downloading information regarding the new calibration material or lot of calibration materials.

In some prior art systems, managing information regarding information regarding calibration materials can be provided in a batch operation which requires transmitting information regarding all possible lots of calibration materials. Even though the information is provided in relatively small files (e.g., pdf-files), the large number of calibration materials and/or lots can result in a data volume of considerable size (e.g., in the terabyte range). Processing an amount of data of this size can result in considerable resource requirements (e.g., of the network connection used to download the data but also for distributing the data in a laboratory or hospital network including the analytical devices for performing in-vitro diagnosis and storage resources). When using the techniques of the present disclosure, the resource requirements can be reduced in some examples. For instance, if a single new lot of a particular calibration material is made available the information for this lot only can be downloaded and distributed.

The technique described above for quality control materials can equally be applied to process information for other reagents or consumables used when operating analytical devices for performing in-vitro diagnosis.

Further Embodiments

A number of embodiments of the techniques for providing data packages of the present disclosure have been discussed in the preceding sections. In addition, the techniques of providing data packages the present disclosure can also be carried out according to the following embodiments.

A method of providing data packages of a plurality of analytical devices in a network of analytical devices including a gateway is presented. The method can comprise sending a data package request including information regarding the analytical devices of the network from the gateway of the network to a remote service platform, receiving from the remote service platform information regarding a plurality of available data packages in reaction to the request, determining, at the gateway, a selection of the plurality of available data packages to be downloaded from the remote service platform specific to the plurality of analytical devices in the network, requesting the selection of the plurality of available data packages from the remote service platform, downloading the requested selection of the plurality of available data packages from the remote service platform, and providing the requested selection of the plurality of available data packages to the plurality of analytical devices to update data of the plurality of analytical devices.

The selection of the plurality of available data packages can be received from the remote service platform as a batch.

The step of determining a selection of the plurality of available data packages can include determining which data packages are required for the plurality of analytical devices in the network. The determining which data packages are required can include determining which data packages are missing on respective ones of the plurality of analytical devices in the network. The determining which data packages are required can include evaluating one or more rules defined at the gateway. The rules are user-defined. The rules can define one or more requirements for the data packages. The requirements can relate to one or more of a source of the data packages.

Each data package can be only downloaded by the gateway once regardless of a number of analytical devices in the network the data package is to be installed on.

The receipt of the data packages can be scheduled at a predetermined time or can happen upon receiving a message.

The method can further comprise maintaining device configuration information of the plurality of analytical devices at the gateway.

The method can further comprise using the device configuration information to select the plurality of available data packages to be downloaded from the remote service platform.

The method can further comprise updating the device configuration information at the gateway after receiving the requested selection of the plurality of available data packages from the remote service platform, optionally after installation of the data packages on the devices.

The method can further comprise providing the updated list of device configurations to a remote location. The remote location can be a location of a distributor of the data packages.

The method can further comprise providing information indicating the received selection of the plurality of available data packages to a remote location. The remote location can be a location of a distributor of the data packages.

The method can further comprise scheduling, at the gateway, a distribution of the received selection of the plurality of available data packages to the plurality of analytical devices according to one or more data package selection or data package distribution rules. The rules can include a rule forcing a staggered distribution of data packages to analytical devices of the same type to ensure that at least one device of the type is available at a given time. The rules can include a rule scheduling a distribution to the analytical devices taking into account an idle state and/or a workload of the analytical devices.

The plurality of analytical devices can include one or more devices for performing in-vitro diagnosis, an IT system device or a research analytical device.

The network of analytical devices can be part of a hospital network, a laboratory network, a network of a general practitioner's cabinet or a network of a pharmacy.

The sending a request for a plurality of applicable data packages from a gateway of the network including the plurality of analytical devices to a remote service platform can be triggered based on a schedule or on demand, or upon receiving a message from the remote service platform.

The method can further comprises evaluating, at the remote service platform, the information regarding the analytical devices to select the information regarding a plurality of available data packages to the gateway.

The information regarding the analytical devices can include one or more of information regarding types of class of the devices, information regarding the geographical location of the network; information regarding a software or hardware configuration of the devices; information regarding a language of the network or the analytical devices; information regarding installed consumables of the devices such as reagents, calibration/quality control materials; and information regarding installed analytical tests (test protocols).

The remote service platform can filter out already installed packages based on the information regarding the analytical devices.

The selection of the plurality of available data packages can include less than all data packages.

Each data package can include an update for the software of a device of the plurality of analytical devices.

A method of providing data packages of a plurality of analytical devices in a network of analytical devices including a gateway is also presented. The method can comprise receiving, at a remote service platform, a data package request including information regarding the analytical devices of the network from the gateway of the network, transmitting from the remote service platform to the gateway information regarding a plurality of available data packages in reaction to the request, receiving, at the remote service platform, a request for a selection of the plurality of available data packages to be downloaded from the remote service platform specific to the plurality of analytical devices in the network, and transmitting the requested selection of the plurality of available data packages to the gateway.

A computer network is also presented. The computer network can comprise a plurality of analytical devices and a gateway connected to the plurality of analytical devices. The computer network can be configured to carry out the steps of the above methods.

A computer system comprising a remote service platform connected to a network, comprising a plurality of analytical devices and a gateway connected to the plurality of analytical devices is also presented. The computer system can be configured to carry out the steps of the above methods.

A computer-readable medium including instructions which when carried out by a computer system can causes the computer system to carry out the steps of the above methods.

A hospital network or a laboratory network including a plurality of analytical devices for performing in-vitro diagnosis and a gateway connected to the plurality of analytical devices is also presented. The network can be configured to send a data package request including information regarding the analytical devices from the gateway to a remote service platform, receive from the remote service platform information regarding a plurality of available data packages in reaction to the request, determine, at the gateway, a selection of the plurality of available data packages to be downloaded from the remote service platform specific to the plurality of analytical devices in the network, request the selection of the plurality of available data packages from the remote service platform, download the requested selection of the plurality of available data packages from the remote service platform, and provide the requested selection of the plurality of available data packages to the plurality of analytical devices to update data of the plurality of analytical devices.

The data packages can include information that can be used in operating the plurality of analytical devices. The data packages can include configuration information for a particular test or assay or information related to a particular consumable. The consumable can be a reagent, a calibration material or a quality control material or other substance required for carrying out tests or assays at the analytical device.

The data packages can include information regarding a particular reagent lot.

The information regarding the analytical devices can include information regarding installed consumables of the devices. The consumables can be reagents, calibration materials or quality control materials.

The network can be further configured to maintain device configuration information of the plurality of analytical devices at the gateway, use the device configuration information to select the plurality of available data packages to be downloaded from the remote service platform.

The network can be further configured to update the device configuration information at the gateway after receiving the requested selection of the plurality of available data packages from the remote service platform, optionally after installation of the data packages on the devices.

The step of determining a selection of the plurality of available data packages can include determining which data packages are required for the plurality of analytical devices in the network. The determining which data packages are required can include determining which data packages are missing on respective ones of the plurality of analytical devices in the network.

Each data package can be only downloaded by the gateway once regardless of a number of analytical devices in the network the data package is to be installed on.

The receipt of the data packages can be scheduled at a predetermined time or can happen upon receiving a message.

The network can be further configured to provide information indicating the received selection of the plurality of available data packages to a remote location. The remote location can be a location of a distributor of the data packages.

The network can be further configured to schedule, at the gateway, a distribution of the received selection of the plurality of available data packages to the plurality of analytical devices according to one or more data package selection or data package distribution rules. The rules can include a rule forcing a staggered distribution of data packages to analytical devices of the same type to ensure that at least one device of the type is available at a given time and/or a rule scheduling a distribution to the analytical devices taking into account an idle state and/or a work load of the analytical devices.

A method of providing data packages of a plurality of devices for performing in-vitro diagnosis in a hospital network or a laboratory network of devices for performing in-vitro diagnosis including a gateway is also presented. The method can comprise sending a data package request including information regarding analytical devices from the gateway of the network to a remote service platform, receiving from the remote service platform information regarding a plurality of available data packages in reaction to the request, determining, at the gateway, a selection of the plurality of available data packages to be downloaded from the remote service platform specific to the plurality of analytical devices in the network, requesting the selection of the plurality of available data packages from the remote service platform, downloading the requested selection of the plurality of available data packages from the remote service platform, and providing the requested selection of the plurality of available data packages to the plurality of analytical devices to update data of the plurality of analytical devices.

A method of providing data packages of a plurality of analytical devices for performing in-vitro diagnosis in a hospital or laboratory network of devices for performing in-vitro diagnosis including a gateway is also presented. The method can comprise receiving, at a remote service platform, a data package request including information regarding the analytical devices from the gateway of the network, transmitting from the remote service platform to the gateway information regarding a plurality of available data packages in reaction to the request, receiving, at the remote service platform, a request for a selection of the plurality of available data packages to be downloaded from the remote service platform specific to the plurality of analytical devices in the network, and transmitting the requested selection of the plurality of available data packages to the gateway.

A computer system comprising a remote service platform connected to a network comprising a plurality of analytical devices and a gateway connected to the plurality of analytical devices is presented. The computer system including a remote service platform can be configured to carry out the steps of the above method.

A computer-readable medium including instructions which when carried out by a computer system can causes the computer system to carry out the steps of the above method.

Computer-Implementation

Further disclosed and proposed is a computer program including computer-executable instructions for performing the method according to the present disclosure in one or more of the embodiments enclosed herein when the program is executed on a computer or computer network. Specifically, the computer program may be stored on a computer-readable data carrier. In other examples, the computer program can be Cloud-based computer programs. Thus, specifically, one, more than one or even all of method steps as disclosed herein may be performed by using a computer or a computer network, preferably by using a computer program.

Further disclosed and proposed is a computer program product having program code, in order to perform the method according to the present disclosure in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal, which can contain instructions readable by a computer system or computer network, for performing the method according to one or more of the embodiments disclosed herein.

Referring to the computer-implemented embodiments of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network (e.g., a Cloud-based computer network). Generally, these method steps may include any of the method steps, typically except for method steps requiring manual work, such as providing the samples and/or certain aspects of performing measurements.

Further disclosed and proposed is a computer, or computer network, comprising at least one processor, wherein the processor is adapted to perform the method according to one of the embodiments described in this description.

Further disclosed and proposed is a computer loadable data structure that is adapted to perform the method according to one of the embodiments described in this description while the data structure is being executed on a computer.

Further disclosed and proposed is a storage medium, wherein a data structure is stored on the storage medium and wherein the data structure is adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A hospital network or a laboratory network, the network comprising:

a plurality of analytical devices for performing in-vitro diagnosis; and a gateway connected to the analytical devices, wherein the network is configured to:

send a data package request including information regarding each of the plurality of analytical devices from the gateway to a remote service platform, the information regarding the analytical devices comprising information regarding a particular laboratory test or assay or installable consumable substance of the devices;

receive from the remote service platform information regarding a plurality of available data packages in reaction to the request, determine, at the gateway, a selection of the plurality of available data packages to be downloaded from the remote service platform specific to the plurality of analytical devices in the network, request the selection of the plurality of available data packages from the remote service platform, download the requested selection of the plurality of available data packages from the remote service platform, and provide the requested selection of the plurality of available data packages to the plurality of analytical devices to update data of the plurality of analytical devices.

2. The network of claim 1, wherein the data packages comprises information that is used in operating the plurality of analytical devices.

3. The network of claim 1, wherein the data packages comprise configuration information for a particular test or assay or information related to a particular consumable.

4. The network of claim 3, wherein the data packages comprise configuration information for a consumable comprising a reagent, a calibration material, a quality control material or another substance required for carrying out tests or assays at the analytical device.

5. The network of claim 1, wherein the data packages comprises information regarding a particular reagent lot.

6. The network of claim 1, wherein the consumables are reagents, calibration materials or quality control materials.

7. The network of claim 1, further configured to:

maintain device configuration information of the plurality of analytical devices at the gateway; and use the device configuration information to select the plurality of available data packages to be downloaded from the remote service platform.

8. The network of claim 7, further configured to:

update the device configuration information at the gateway after receiving the requested selection of the plurality of available data packages from the remote service platform after installation of the data packages on the devices.

9. The network of claim 1, wherein the determination of a selection of the plurality of available data packages comprises determining which data packages are required for the plurality of analytical devices in the network.

10. The network of claim 9, wherein the determining which data packages are required includes determining which data packages are missing on each of the plurality of analytical devices in the network.

11. The network of claim 1, wherein each data package is only downloaded by the gateway once regardless of a number of analytical devices in the network the data package is to be installed on.

12. The network of claim 1, wherein the receipt of the data packages is scheduled at a predetermined time or happens upon receiving a message.

13. The network of claim 1, further configured to:
provide information indicating the received selection of the plurality of available data packages to a remote location.

14. The network of claim 13, wherein the remote location is a location of a distributor of the data packages.

15. The network of claim 1, further configured to:
schedule, at the gateway, a distribution of the received selection of the plurality of available data packages to the plurality of analytical devices according to one or more data package selection or data package distribution rules, wherein the rules include a rule forcing a staggered distribution of data packages to analytical devices of the same type to ensure that at least one device of the type is available at a given time and/or a rule scheduling a distribution to the analytical devices taking into account an idle state and/or a work load of the analytical devices.

16. A method of providing data packages to a plurality of devices for performing in-vitro diagnosis in a hospital network or a laboratory network of devices for performing in-vitro diagnosis including a gateway, the method comprising:
sending a data package request including information regarding each of the plurality of analytical devices from the gateway of the network to a remote service platform, the information regarding the analytical devices comprising information regarding a particular laboratory test or assay or installable consumable substance of the devices;
receiving from the remote service platform information regarding a plurality of available data packages in reaction to the request;
determining, at the gateway, a selection of the plurality of available data packages to be downloaded from the remote service platform specific to the plurality of analytical devices in the network;
requesting the selection of the plurality of available data packages from the remote service platform;
downloading the requested selection of the plurality of available data packages from the remote service platform; and
providing the requested selection of the plurality of available data packages to the plurality of analytical devices to update data of the plurality of analytical devices.

17. A method of providing data packages of a plurality of analytical devices for performing in-vitro diagnosis in a hospital or laboratory network of analytical devices including a gateway, the method comprising:
receiving, at a remote service platform, a data package request including information regarding each of the plurality of analytical devices from the gateway of the network, the information regarding the analytical devices comprising information regarding a particular laboratory test or assay or installable consumable substance of the devices;
transmitting from the remote service platform to the gateway information regarding a plurality of available data packages in reaction to the request;
receiving, at the remote service platform, a request for a selection of the plurality of available data packages to be downloaded from the remote service platform specific to the plurality of analytical devices in the network; and
transmitting the requested selection of the plurality of available data packages to the gateway.

18. A computer system, the computer system comprising:
a remote service platform connected to a network comprising a plurality of analytical devices and a gateway connected to the plurality of analytical devices and configured to carry out the method of claim 17.

19. A non-transitory computer-readable medium including instructions which when carried out by a computer system causes the computer system to carry out the method of claim 16.

* * * * *